United States Patent [19]

Meier et al.

[11] Patent Number: 5,756,757

[45] Date of Patent: May 26, 1998

[54] PROCESS FOR THE PREPARATION OF 3-HYDROXY-N-BENZIMIDAZOLON-5-YL-2-NAPHTHAMIDE IN THE HIGH PURITY REQUIRED OF AZO PIGMENTS

[75] Inventors: Michael Meier, Frankfurt am Main; Heinrich Volk, Bad Vilbel; Rudolf Neeb, Offenbach, all of Germany

[73] Assignee: Hoechst Aktiengesellschaft, Frankfurt, Germany

[21] Appl. No.: 559,551

[22] Filed: Nov. 16, 1995

[30] Foreign Application Priority Data

Nov. 18, 1994 [DE] Germany .................. 44 41 146.6

[51] Int. Cl.⁶ ............................................. C07D 235/26
[52] U.S. Cl. ............................................. 548/306.4
[58] Field of Search ................................ 548/306.4

[56] References Cited

FOREIGN PATENT DOCUMENTS

| | | |
|---|---|---|
| 178560 | 5/1979 | Czechoslovakia . |
| A-2747 | 7/1979 | European Pat. Off. . |
| 265894 | 3/1989 | German Dem. Rep. . |
| 2758818 | 7/1979 | Germany . |
| 119895 | 9/1983 | Poland . |
| 144734 | 1/1989 | Poland . |

OTHER PUBLICATIONS

Kraska, J. et al, *Dyes and Pigments 12*: "Synthesis of Amides of 3-Hydroxy-2-Naphthoic Acid: Derivatives of Benzimidazolone and Benzoxazolone", pp. 57–63 (1990).

Chemical Abstract, vol. 92, No. 9, Abstract No. 76179k, p. 741, Mar. 3, 1980.

Chemical Abstract, vol. 112, No. 13, Abstract No. 118816e, p. 647, Mar. 26, 1990.

M. Vata et al, "Unkonventionelle Syntheses des 5–Amino–Benzimidazolon–(2)–naphtharylids", *Revue Roumaine De Chimie*, pp. 719–722, Jun. 6, 1992.

*Primary Examiner*—Johann Richter
*Assistant Examiner*—Laura L. Stockton
*Attorney, Agent, or Firm*—Connolly & Hutz

[57] ABSTRACT

The invention relates to a process for the preparation of 3-hydroxy-N-benzimidazolon-5-yl-2-naphthamide, which comprises reacting 5-aminobenzimidazolone and sodium carbonate in N-methylpyrrolidone with a solution of 3-hydroxy-2-naphthoyl chloride in xylene or toluene, filtering, washing with xylene or toluene, introducing the filter cake into water to which sodium carbonate has been added and steam-distilling, filtering off the residue with suction, washing and drying.

18 Claims, No Drawings

PROCESS FOR THE PREPARATION OF 3-HYDROXY-N-BENZIMIDAZOLON-5-YL-2-NAPHTHAMIDE IN THE HIGH PURITY REQUIRED OF AZO PIGMENTS

Process for the preparation of 3-hydroxy-N-benzimidazolon-5-yl-2-naphthamide in the high purity required of azo pigments The invention relates to a process for the preparation of 3-hydroxy-N-benzimidazolon-5-yl-2-naphthamide in the high purity required of azo pigments by reaction of 3-hydroxy2-naphthoic acid in toluene or xylene with thionyl chloride and subsequent condensation with 5-aminobenzimidazolone in N-methylpyrrolidone in the presence of sodium carbonate.

3-Hydroxy-N-benzimidazolon-5-yl-2-naphthamide is an important intermediate for the preparation of azo pigments of high fastness.

It has been disclosed that 3-hydroxy-N-benzimidazolon-5yl-2-naphthamide can be prepared by reaction of 3-hydroxy-2-naphthoic acid and 5-aminobenzimidazolone in N-methylpyrrolidone with phosphorus trichloride at temperatures of 105°–150° C. in 84% yield in a yellow modification which is fit for azo pigments (DE 2758818). It has also been disclosed that 3-hydroxy-N-benzimidazolon-5-yl-2-naphthamide can be prepared by reaction of a large excess of 3-hydroxy-2-naphthoic acid and 5-aminobenzimidazolone in xylene with phosphorus trichloride in 84% yield (DD 265894). A disadvantage of this process is that the excess 3-hydroxy-2-naphthoic acid has to be recovered again, whereby the process becomes economically unfavorable. A phosphorus-containing effluent is formed in both processes.

CS 178560 describes the reaction of a solution of 3-hydroxy-2-naphthoyl chloride in toluene with 5-aminobenzimidazolone in the 30-fold amount of water in the presence of sodium acetate to give 3-hydroxy-N-benzimida-zolon-5-yl-2-naphthamide in 86% yield.

A disadvantage of this process is the large reaction volumes.

The reaction of stoichiometric amounts of 3-hydroxy-2naphthoyl chloride and 5-aminobenzimidazoles in organic acids in the presence of the sodium or potassium salts of these acids has been disclosed (Polish P 119895). An improvement of this method of preparation consists in the replacement of the organic acids by N,N'-dimethylformamide or N-methylpyrrolidone (Polish P 144734 and Dyes and Pigments 12, 57-63 (1990)). The 3-hydroxy-N-benzimidazolon-5-yl-2-naphthamide prepared by this preparation method does not meet the requirements for azo pigments, as the product still contains too much starting material (see Comparison Example 1). A further disadvantage of this process are the long suction times during the isolation of the products (see Comparison Example 1).

In most of the abovementioned processes 3-hydroxy-N-benzimidazolon-5-yl-2-naphthamide is not formed in the high purity required of azo pigments. For the preparation of azo pigments of high fastness, as described in DE 2758818, these products must therefore be purified via the alkali metal salt.

There was therefore a need for a process which can be carried out easily scientifically and industrially for the preparation of 3-hydroxy-N-benzimidazolon-5-yl-2naphthamide in a very high purity for the preparation of azo pigments of high fastness.

This object is achieved by a process for the preparation of 3-hydroxy-N-benzimidazolon-5-yl-2-naphthamide, which comprises reacting 5-aminobenzimidazolone and sodium carbonate in N-methylpyrrolidone with a solution of 3-hydroxy-2-naphthoyl chloride in xylene or toluene, filtering, washing with xylene or toluene, introducing the filter cake into water to which sodium carbonate has been added and steam-distilling, filtering off the residue with suction, washing and drying.

3-Hydroxy-2-naphthoyl chloride is prepared in a manner known per se from 1 mol of 3-hydroxy-2-naphthoic acid in about 5 parts by volume of xylene or toluene per part of 3-hydroxy-2-naphthoic acid by reaction with 1.05 mol of thionyl chloride with addition of a catalyst, for example N,N'-dimethylformamide, pyridine or triethylamine, at 47°–50° C. The solution prepared in this way is further reacted with 5-aminobenzimidazolone.

Customarily, the procedure in the preparation of 3-hydroxy-N-benzimidazolon-5-yl-2-naphthamide is to initially introduce 5-aminobenzimidazolone and sodium carbonate in N-methylpyrrolidone and to meter in a solution of 3-hydroxy-2-naphthoyl chloride in xylene or toluene in the course of 4 to 10 h. The mixture is then filtered, and the filter cake is washed with xylene or toluene and introduced into water, sodium carbonate is added and the mixture is distilled. The solid is again filtered off with suction, and the filter cake is preferably washed with water until neutral and dried.

5-Aminobenzimidazolone is employed in an amount of from 0.9 to 1 mol, in particular 0.95 mol, per mole of 3-hydroxy-2-naphthoic acid.

Sodium carbonate is employed in an amount of from 0.8 to 1.8, in particular 1.0 to 1.3, mol per mole of 3-hydroxy2-naphthoic acid.

N-Methylpyrrolidone is used in 3 to 6, in particular 4 to 5, parts by volume per part of 5-aminobenzimidazolone.

The reaction of the solution of 3-hydroxy-2-naphthoyl chloride in xylene or toluene with 5-aminobenzimidazolone is carried out at 15° to 40° C., in particular 20° to 35° C.

The steam distillation is advantageously carried out using 5 to 7 parts of water and 0.5 to 0.6 parts of sodium carbonate per part of 5-aminobenzimidazolone.

By means of the steam distillation it is surprisingly possible to separate off the impurities such that the residue after filtering off with suction and washing with water is very pure target product.

The addition time of the 3-hydroxy-2-naphthoyl chloride is important for the purity of the resulting product. In order to obtain 3-hydroxy-N-benzimidazolon-5-yl-2-naphthamide in the necessary pigment purity, the addition time should be at least 2 h, in particular 4 h, preferably between 4 and 10 h. It is also possible to choose a longer addition time than 10 h, but there is thus no advantage with respect to the purity.

According to the abovementioned process, 3-hydroxy-N-benzimidazolon-5-yl-2-naphthamide can be prepared in 85% yield and in the very high purity which is necessary for the preparation of azo pigments of high fastness. A further purification, such as in the prior art, can be dispensed with.

EXAMPLE 1

3-Hydroxy-2-naphthoyl chloride in xylene 494.0 g (2.63 mol) of 3-hydroxy-2-naphthoic acid and 2470.0 g=2872 ml of xylene are initially introduced into a 2 l four-necked flask having an internal thermometer, gas removal tube and stirrer, 6.0 g of N,N'-dimethylformamide are added, 328.0 g=201.1 ml (2.76 mol) of thionyl chloride are metered in at 47°–50°0C. over the course of 1 h and the mixture is subsequently stirred for 3 h until evolution of gas has ended. 3181.8 g of 3-hydroxy-2-naphthoyl chloride are obtained as a clear solution in xylene.

3-Hydroxy-N-benzimidazolon-5-yl-2-naphthamide 1750 ml of N-methylpyrrolidone are initially introduced into a 10 l four-necked flask having a dropping funnel, reflux condenser, internal thermometer and stirrer. 291.5 g (2.75 mol) of sodium carbonate are added to this. 372.5 g (2.5 mol) of 5-aminobenzimidazolone are then added at about 25° C. 3181.8 g of 3-hydroxy-2-naphthoyl chloride (from 494.0 g (2.63 mol) of 3-hydroxy-2naphthoic acid) in xylene are metered into the suspension thus obtained with stirring in the course of 6.5 h at 25°–28° C. After addition is complete, the mixture is subsequently stirred at room temperature for 30 min. The precipitated product is filtered off with suction (suction time: 50 min) and the filter cake is washed in 10 portions with a total of 2150.0 g=2500 ml of xylene. 2500 ml of water are initially introduced into a 6 l four-necked flask having a stirrer, internal thermometer and distillation bridge having a 1 l one-necked flask as a receiver. The filter cake is then introduced. 200.0 g of sodium carbonate are then added and the mixture is heated to 100° C. Xylene and water distill off. The product is filtered off with suction at 100° C. and the suction filter cake is washed several times with a total of 6250 ml of water until neutral. 1571.4 g of naphthalone are obtained in water-moist form. After drying the filter cake at 100° C./100 mmHg, 681.7 g (2.135 mol) of 3-hydroxy-N-benzimidazolon-5-yl-2naphthamide are obtained; this corresponds to a yield of 85.4% of theory based on 5-aminobenzimidazolone.

The product thus obtained is fit for the preparation of azo pigments of high fastness and according to HPLC contains <0.1% of 5-aminobenzimidazolone and <0.1% of 3-hydroxy-2-naphthoic acid.

Comparison Example 1 (Example from Dyes and Pigments 12, 57–63 (1990)):

3-Hydroxy-2-naphthoyl chloride in chlorobenzene 99.0 g (0.52 mol) of 3-hydroxy-2-naphthoic acid and 1 ml of N,N'-dimethylformamide are initially introduced into 600 ml of chlorobenzene and 68.5 g=42 ml (0.58 mol) of thionyl chloride are added at 40° C. The mixture is subsequently stirred at 40° C. for 1.5 h and excess thionyl chloride is then distilled off in vacuo. 776.8 g of 3-hydroxy-2-naphthoyl chloride are obtained as a clear solution in chlorobenzene.

3-Hydroxy-N-benzimidazolon-5-yl-2-naphthamide 75.0 g (0.5 mol) of 5-aminobenzimidazolone and 41 g of anhydrous sodium acetate are initially introduced into 700 ml of N,N'-dimethylformamide and 776.8 g of 3-hydroxy-2-naphthoyl chloride (from 99.0 g (0.52 mol) of 3-hydroxy-2-naphthoic acid) in chlorobenzene are metered in at 5°–10° C. in the course of 30 min. After addition is complete, the mixture is subsequently stirred at 20° C. for 3 h, warmed to 50° C. and filtered. The filter cake does not filter off with suction very well (suction time: 14 h). For purification, the filter cake is taken up in 1 ml of methanol, the mixture is stirred and filtered off with suction, and the filter cake is washed with 250 ml of methanol and subsequently several times with a total of 1 l of boiling water. After drying, 130.3 g of 3-hydroxy-N-benzimidazolon-5-yl-2-naphthamide are obtained; this corresponds to 81.7% of theory.

The product thus obtained cannot be used for the preparation of azo pigments of high fastness and according to HPLC contains about 0.1% of 5-aminobenzimidazolone and about 0.8% of 3-hydroxy-2-naphthoic acid and is additionally contaminated.

We claim:

1. A process for the preparation of 3-hydroxy-N-benzimidazolon5-yl-2-naphthamide which comprises reacting 5-aminobenzimidazolone and sodium carbonate in N-methylpyrrolidone with 3-hydroxy-2-naphthoyl chloride dissolved in xylene or toluene, wherein said 3-hydroxy-2-naphthoyl chloride being obtained by reacting 3-hydroxy-2-naphtoic acid with thionylchloride in xylene or toluene while employing the 5-amino-benzimidazolone in an amount of from 0.9 to 1 mol. per mol of 3-hydroxy-2-naphthoic acid, filtering the product formed, washing with xylene or toluene introducing the filter cake into water to which sodium carbonate has been added and steam-distilling, filtering off the residue with suction, washing and drying.

2. The process as claimed in claim 1, wherein sodium carbonate is employed in an amount of from 0.8 to 1.8 mol per mole of 3-hydroxy-2-naphthoic acid.

3. The process as claimed in claim 1, wherein N-methylpyrrolidone is used in 3 to 6 parts by volume per part of 5-aminobenzimidazolone.

4. The process as claimed in claim 1, wherein the reaction of the solution of 3-hydroxy-2-naphthoyl chloride in xylene or toluene with 5-aminobenzimidazolone is carried out at 15° to 40° C.

5. The process as claimed in claim 1, wherein 5-aminobenzimidazolone and sodium carbonate are initially introduced in N-methylpyrrolidone and the solution of 3-hydroxy-2-naphthoyl chloride in toluene or xylene is metered in.

6. The process as claimed in claim 5, wherein the addition time is at least 2 hours.

7. The process as claimed in claim 1 wherein the steam distillation is carried out using 5 to 7 parts of water and 0.5 to 0.6 parts of sodium carbonate per part of 5-aminobenzimidazolone.

8. The process as claimed in claim 1 wherein 5-aminobenzimidazolone is employed in an amount of 0.95 mol per mole of 3-hydroxy-2-naphthoic acid.

9. The process as claimed in claim 2, wherein sodium carbonate is employed in an amount of from 1.0 to 1.3 mol per mole of 3-hydroxy-2-naphthoic acid.

10. The process as claimed in claim 3, wherein the N-methylpyrrolidone is used in 4 to 5 parts by volume per part of 5-aminobenzimidazolone.

11. The process as claimed in claim 4, wherein the reaction of the solution of 3-hydroxy-2-naphthoyl chloride in xylene or toluene with 5-aminobenzimidazolone is carried out at 20° to 35° C.

12. The process as claimed in claim 6, wherein the addition time is at least 4 hours.

13. The process as claimed in claim 12, wherein the addition time is from 4 to 10 hours.

14. A process for the preparation of 3-hydroxy-N-benzimidazolon5-yl-2-naphthamide which comprises reacting 5-aminobenzimidazolone and sodium carbonate in N-methylpyrrolidone with a solution which comprises 3hydroxy-2-naphthoyl acid in xylene or toluene at a temperature from 15° to 40° C., filtering, washing with xylene or toluene, introducing the filter cake into water to which sodium carbonate has been added and steam-distilling, filtering off the residue with suction, washing and drying and wherein the addition time is at least 2 hours, wherein 5-amino-benzimidazolone is employed in an amount of from 0.9 to 1 mol. per mol of 3-hydroxy-2-naphthoic acid.

15. The process as claimed in claim 14, wherein N-methylpyrrolidone is used in 3 to 6 parts by volume per part of 5-aminobenzimidazolone.

16. The process as claimed in claim 15, wherein 5-aminobenzimidazolone is employed in an amount of 0.95 mol per mole of 3-hydroxy-2-naphthoic acid.

17. The process as claimed in claim 16, wherein the addition time is at least 4 hours.

18. The process as claimed in claim 17, wherein the addition time is from 4 to 10 hours.

* * * * *